United States Patent [19]

Neubauer et al.

[11] Patent Number: 4,960,796
[45] Date of Patent: * Oct. 2, 1990

[54] CYCLOPROPANECARBOXAMIDES

[75] Inventors: Hans-Juergen Neubauer, Mannheim; Rainer Buerstinghaus, Telgte; Christoph Kuenast, Otterstadt; Peter Hofmeister, Neustadt, all of Fed. Rep. of Germany

[73] Assignee: BASF Aktiengesellschaft, Ludwigshafen, Fed. Rep. of Germany

[*] Notice: The portion of the term of this patent subsequent to Aug. 22, 2006 has been disclaimed.

[21] Appl. No.: 176,742

[22] Filed: Apr. 1, 1988

[30] Foreign Application Priority Data

Apr. 3, 1987 [DE] Fed. Rep. of Germany ....... 3711268

[51] Int. Cl.$^5$ .................. A01N 53/00; C07C 233/60; C07C 323/40
[52] U.S. Cl. .................................. 514/624; 564/190
[58] Field of Search ............... 564/190, 207, 212, 219; 514/624

[56] References Cited

U.S. PATENT DOCUMENTS

| | | | |
|---|---|---|---|
| 4,048,327 | 9/1977 | Karrer | 424/305 |
| 4,080,470 | 3/1978 | Karrer | 424/300 |
| 4,125,139 | 7/1980 | Fischer et al. | 424/300 |
| 4,166,735 | 9/1979 | Pilgram et al. | 71/118 |
| 4,309,433 | 1/1982 | Hirai et al. | 564/190 |
| 4,859,706 | 8/1989 | Buerstinghaus et al. | 514/624 |

FOREIGN PATENT DOCUMENTS

| | | |
|---|---|---|
| 0004334 | 3/1979 | European Pat. Off. . |
| 0169169 | 1/1986 | European Pat. Off. . |
| 2633069 | 2/1977 | Fed. Rep. of Germany . |
| 2637395 | 2/1977 | Fed. Rep. of Germany . |
| 3211988 | 10/1982 | Fed. Rep. of Germany . |

OTHER PUBLICATIONS

Chemical Abstracts; 109: 376176, Aug. 1, 1988.
European Search Report.

*Primary Examiner*—Carolyn S. Elmore
*Attorney, Agent, or Firm*—Keil & Weinkauf

[57] ABSTRACT

Cyclopropanecarboxamides of the general formula I

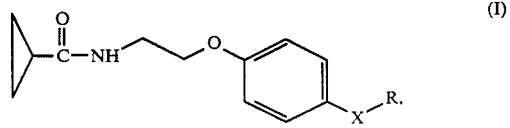

where R is $C_1$–$C_{12}$-alkyl, $C_2$–$C_{12}$-alkenyl, $C_2$–$C_{12}$-alkynyl, $C_1$–$C_{12}$-haloalkyl, $C_2$–$C_{12}$-haloalkenyl, $C_2$–$C_{12}$-haloalkynyl, $C_3$–$C_{12}$-alkoxyalkyl, $C_3$–$C_8$-cycloalkyl, $C_4$–$C_{12}$-cycloalkylalkyl, $C_3$–$C_8$-halocycloalkyl, $C_4$–$C_{12}$-halocycloalkylalhaloalkyl $C_4$–$C_{12}$-cycloalkylhaloalkyl or $C_4$–$C_{12}$-halocycloalkylhaloalkyl and X is oxygen or sulfur.

The present invention furthermore relates to the preparation of the compounds I, pesticides which contain the compounds I, and a method for controlling pests.

5 Claims, No Drawings

CYCLOPROPANECARBOXAMIDES

The present invention relates to novel cyclopropanecarboxamides of the general formula I

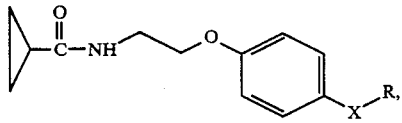 (I)

where R is $C_1$–$C_{12}$-alkyl, $C_2$–$C_{12}$-alkenyl, $C_2$–$C_{12}$-alkynyl, $C_1$–$C_{12}$-haloalkyl, $C_2$–$C_{12}$-haloalkenyl, $C_2$–$C_{12}$-haloalkynyl, $C_3$–$C_{12}$-alkoxyalkyl, $C_3$–$C_8$-cycloalkyl, $C_4$–$C_{12}$-cycloalkylalkyl, $C_3$–$C_8$-halocycloalkyl, $C_4$–$C_{12}$-halocycloalkylalkyl, $C_4$–$C_{12}$-cycloalkylhaloalkyl or $C_4$–$C_{12}$-halocycloalkylhaloalkyl and X is oxygen or sulfur.

The present invention furthermore relates to the preparation of the compounds I, pesticides which contain the compounds I and a method for controlling pests.

The cyclopropanecarboxylate I'

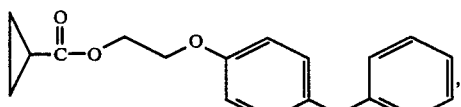 (I')

is disclosed as a pesticide in DE-A No. 26 33 069 and the compound $I^{II}$

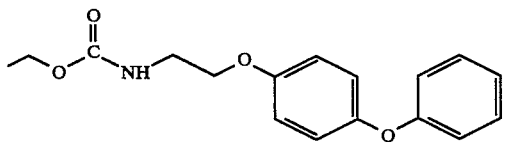 ($I^{II}$)

is disclosed as a pesticide in EP-A-4334. Furthermore, EP-A-169 169 discloses that the compound $I^{III}$

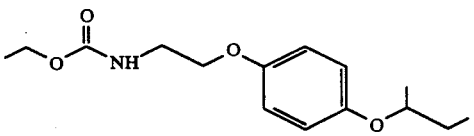 ($I^{III}$)

is a pesticide, and DE-A-26 37 395 discloses that the compound $I^{IV}$

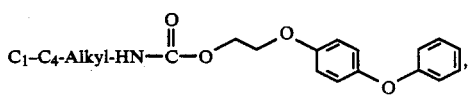 ($I^{IV}$)

is a pesticide and plant growth regulator.

However, the action of the stated compounds is unsatisfactory.

Compounds of the structure $I^V$

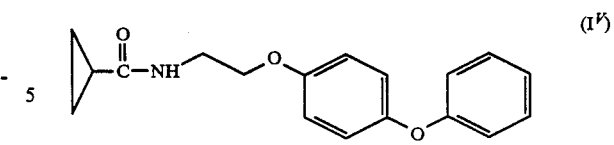 ($I^V$)

have been described by R. Zurfluh and S. Dorn in Abstracts, The Sixth International Congress of Pesticide Chemistry (IUPAC), 2A-01, Aug. 1986, Canada. The aromatic phenoxyphenyl unit is essential for the insecticidal activity. Such compounds are also disclosed in the European Application No. 87 111 934.3.

It is an object of the present invention to provide novel cyclopropanecarboxamides I having an improved action and/or compounds I which are more effective against other pests.

We have found that this object is achieved by the novel cyclopropanecarboxamides I defined at the outset and processes for their preparation. It has also been found that the compounds I are very suitable as pesticides.

The compounds I are obtainable from 2-phenoxyethylamines II and cyclpropanecarbonyl halides III.

The reaction of a 2-phenoxyethylamine II with a cyclopropanecarbonyl halide III, preferably the chloride of III,

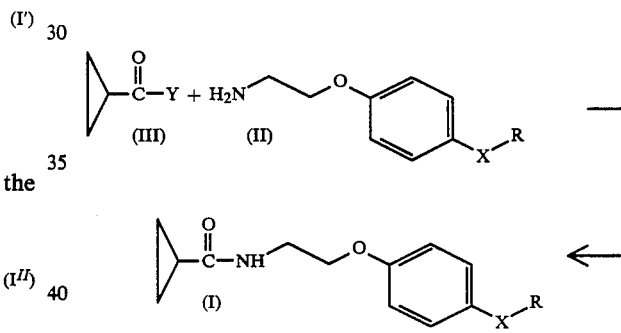

in the presence of an acid acceptor at from −30° to 120° C., preferably from −10° to 80° C., particularly preferably from 0° to 50° C., and under from 1 to 10 bar leads to the cyclopropanecarboxamides I. A suitable acid acceptor is 2-phenoxyethylamine, but the conventional basic agents are usually used, in particular aliphatic, aromatic or heterocyclic amines, for example triethylamine, dimethylamine, piperidine, dimethylaniline, dimethylbenzylamine, pyridine and 4-dimethylaminopyridine. The ratio of acid acceptor to compound III is from 0.5:1 to 20:1, preferably from 0.7:1 to 5:1, particularly preferably from 0.9:1 to 1.5:1.

The starting materials II and III are usually used in a stoichiometric ratio. An excess of one or other component may be quite advantageous in specific cases.

The reaction usually takes place at a sufficient velocity above −30° C. In general, it is not necessary to exceed 100° C. Since in some cases it takes place with evolution of heat, it may be advantageous to provide a means of cooling.

Some of the 2-phenoxyethylamines II are known; those which are unknown can be prepared by a conventional method (EP-A1-4334). Among the cyclopropanecarbonyl halides III, such as the fluoride, chloride or bromide, the chloride is commercially available.

The reactions are advantageously carried out in a solvent or diluent. Examples of suitable solvents or diluents are aliphatic and aromatic hydrocarbons and chlorohydrocarbons, such as petroleum ether, benzene, toluene, xylene, gasoline, dichloromethane, chloroform, tetrachloromethane, 1,2-dichloromethane and chlorobenzene, ethers and esters, such as diethyl and di-n-butyl ether, methyl tert-butyl ether, tetrahydrofuran, dioxane and ethyl acetate, ketones, for example acetone, methyl ethyl ketone and methyl isopropyl ketone, nitriles, such as acetonitrile and propionitrile, and aprotic dipolar solvents, such as dimethylformamide, dimethyl sulfoxide and pyridine. Mixtures of these substances can also be used as solvents or diluents.

Some of the novel compounds of the formula I are obtained in the form of colorless or pale brownish oils, which can be freed from the final volatile constituents by prolonged heating at moderately elevated temperatures under reduced pressure (incipient distillation) and can be purified in this manner. If the compounds of the formula I are obtained in crystalline form, they can be purified by recrystallization.

The novel compounds of the formula I can also be prepared by virtually any known method of carboxamide synthesis, for example by reacting a 2-phenoxyethylamine with an appropriate carboxylate, carboxylic acid or one of its salts, anhydrides or ketene derivatives (cf. C. Ferri, Reaktionen der Organischen Synthese, Georg Thieme Verlag, Stuttgart 1978, page 542, and the literature cited therein).

In the compounds I, R is:

straight-chain or branched $C_1$–$C_{12}$-alkyl, preferably $C_1$–$C_8$-alkyl, particularly preferably branched $C_3$–$C_8$-alkyl, such as isopropyl, isobutyl, sec-butyl, tert-butyl, isopentyl, 1-methylbutyl, isohexyl, 1-methylpentyl, isoheptyl, 1-methylhexyl, 1-methylheptyl, 1,3-dimethylbutyl, 1,2-dimethylbutyl, 3-methylpent-1-yl, 4-methylbut-1-yl, 1-ethylprop-1-yl or 1-ethylbut-1-yl, straight-chain or branched $C_2$–$C_{12}$-alkenyl, preferably $C_2$–$C_8$-alkenyl, particularly preferably $C_3$–$C_6$-alkenyl, such as allyl, 1-methylallyl, 1,3-dimethylbut-2-enyl, 1-methylbut-2-enyl or but-3-en-1-yl, straight-chain or branched $C_2$–$C_{12}$-alkynyl, preferably $C_2$–$C_8$-alkynyl, particularly preferably $C_2$–$C_4$-alkynyl, such ethynyl, prop-1-yn-1-yl, prop-2-yn-1-yl, 1-methylprop-2-ynyl, but-2-yn-1-yl or but-3-yn-1-yl, straight-chain or branched $C_1$–$C_{12}$-haloalkyl, preferably $C_1$–$C_4$-haloalkyl, particularly preferably $C_1$–$C_4$-fluoro- or chloroalkyl, such as trifluoromethyl, difluoromethyl, fluoromethyl, trichloromethyl, pentafluoroethyl, 2,2,2-trifluoroeth-1-yl, 2,2,2-trichloroeth-1-yl, 1-fluoromethyl-2-fluoroethyl or 1-chloromethyl-2-chloroethyl, straight-chain or branched $C_2$–$C_{12}$-haloalkenyl, preferably $C_2$–$C_4$-haloalkenyl, particularly preferably $C_2$–$C_4$-fluoro- or chloroalkenyl, such as 1,2,2-trifluoroethen-1-yl, 1,2,2-trichloroethen-1-yl, 3,3-difluoroprop-2-en-1-yl or 3,3-dichloroprop-2-en-1-yl, straight-chain or branched $C_2$–$C_{12}$-haloalkynyl, preferably $C_2$–$C_4$-haloalkynyl, particularly preferably $C_2$–$C_4$-fluoro- or chloroalkynyl, such as fluoroethynyl, chloroethynyl, 3-fluoroprop-2-yn-1-yl or 3-chloroprop-2-yn-1-yl, straight-chain or branched $C_3$–$C_{12}$-alkoxyalkyl, preferably $C_3$–$C_9$-alkoxyalkyl, particularly preferably $C_1$–$C_4$-alkoxy-substituted $C_1$–$C_5$-alkoxyalkyl, for example 2-methoxyethyl, 2-methoxyprop-1-yl, 3-methoxyprop-2-yl, 3-methoxybut-1-yl, 4-methoxybut-2-yl, 4-methoxybut-3-yl, 5-methoxypent-3-yl, 2-ethoxyethyl, 2-ethoxyprop-1-yl, 3-ethoxyprop-1-yl, 3-ethoxybut-1-yl, 3-ethoxybut-2-yl, 5-ethoxypent-2-yl, 2-propoxyethyl, 2-propoxyprop-1-yl, 3-propoxybut-1-yl, butoxymethyl or 2-butoxyprop-2-yl, $C_2$–$C_8$-cycloalkyl, preferably $C_3$–$C_6$-cycloalkyl, such as cyclopropyl, cyclobutyl, cyclopentyl or cyclohexyl, $C_4$–$C_{12}$-cycloalkylalkyl, preferably $C_4$–$C_8$-cycloalkylalkyl, such as cyclopropylmethyl, cyclopropylethyl, cyclobutylmethyl, cyclopentylmethyl, cyclohexylmethyl or cyclohexylethyl, $C_3$–$C_8$-halocycloalkyl, preferably $C_3$–$C_6$-halocycloalkyl, particularly preferably $C_3$–$C_6$-fluoro- or chlorocycloalkyl, such as 2,2-difluoroprop-1-yl or 2,2-dichlorocycloprop-1-yl, $C_4$–$C_{12}$-halocycloalkylalkyl, preferably $C_4$–$C_8$-halocycloalkylalkyl, particularly preferably $C_4$–$C_8$-fluoro- or chlorocycloalkylalkyl, such as 2,2-difluorocycloprop-1-yl-methyl or 2,2-dichlorocycloprop-1-yl methyl, $C_4$–$C_{12}$-cycloalkylhaloalkyl, preferably $C_4$–$C_8$-cycloalkylhaloalkyl, particularly preferably $C_4$–$C_8$-cycloalkylfluoro- or -chloroalkyl, such as 2-cyclopropyl-2-chloroethyl or 2-cyclopropyl-1,1-difluoroethyl, $C_4$–$C_{12}$-halocycloalkylhaloalkyl, preferably $C_4$–$C_8$-halocycloalkylhaloalkyl, particularly preferably $C_4$–$C_8$-fluoro- or chlorocycloalkylfluoro- or -chloroalkyl, such as 2,2-dichlorocycloprop-1-yl-2-chloroethyl.

Among the radicals X, oxygen is preferred.

The novel compounds I may contain one or more centers of asymmetry in the substituent R. The present invention includes all possible stereoisomers, diastereomers, enantiomers and diastereomer and enantiomer mixtures. The relevant compounds in the Table of the exemplary compounds are the particular racemic mixtures.

In contrast to most of the pesticides known to date, which act as contact or ingested poisons and kill, incapacitate or repel the animals, the compounds of the formula I intervene in the hormonal system of the animal organism. In the case of insects, for example, the transformation to the imago, the laying of viable eggs and the development of normal laid eggs are disturbed and hence the sequence of generations interrupted. The novel agents are virtually completely non-toxic for vertebrates. The compounds of the formula I are furthermore readily degraded to give substances which occur in nature and are further decomposed by microorganisms. There is therefore no danger of accumulation. Accordingly, they can safely be used for controlling pests in animals, crops and stored materials and in water.

The cyclopropanecarboxamides I in which R is a branched alkyl, alkenyl, alkynyl or alkoxyalkyl radical which carries a methyl group in the 1-position and X is oxygen have proven particularly effective.

The cyclopropanecarboxamides of the formula I are suitable for effectively combating pests from the class of insects, Arachnida and nematodes. They may be used for protecting crop plants, and in the hygiene, stores protection and veterinary sectors as pesticides.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana,*

Tortrix viridana, Clysia ambiguella, Evetria buoliana, Polychrosis botrana, Cydia pomonella, Laspeyresia molesta, Laspeyresia funebra, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus pinarius, Hyphantria cunea, Agrotis segetum, Agrotis ypsilon, Barathra brassicae, Cirphis unipuncta, Prodenia litura, Laphygma exigua, Panolis flammea, Earis insulana, Plusia gamma, Alabama argillacea, Lymantria dispar, Lymantria monacha, Pieris brassicae, and Aporia crataegi;

examples from the Coleoptera order are Blitophaga undata, Melanotus communis, Limonius californicus, Agriotes lineatus, Agriotes obscurus, Agrilus sinuatus, Meligethes aeneus, Atomaria linearis, Epilachna varicestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus, and Blastophagus piniperda;

examples from the Diptera order are Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata, and Hypoderma lineata;

examples from the Hymenoptera order are Athalia rosae, Hoplocampa minuta, Monomorium pharaonis, Solenopsis geminata, and Atta sexdens;

examples from the Heteroptera order are Nezara viridula, Eurygaster integriceps, Blissus leucopterus, Dysdercus cingulatus, Dysdercus intermedius, Piesma quadrata, and Lygus pratensis;

examples from the Homoptera order are Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis, and Viteus vitifolii;

examples from the Isoptera order are Reticulitermes lucifugus, Calotermes flavicollis, Leucotermes flavipes, and Termes natalensis;

examples from the Orthoptera order are Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana, and Blabera gigantea.

Examples of mites and ticks (Acarina) belonging to the Arachnida class are Tetranychus telarius, Tetranychus pacificus, Paratetranychus pilosus, Bryobia praetiosa, Ixodes ricinus, Ornithodorus moubata, Amblyomma americanum, Dermacentor silvarum, and Boophilus microplus.

Examples from the Nemathelminthes class are root-knot nematodes, e.g., Meloidogyne incognita, Meloidogyne hapla, and Meloidogyne javanica, cyst-forming nematodes, e.g., Heterodera rostochiensis, Heterodera schachtii, Heterodera avenae, Heterodera glycines and Heterodera trifolii, and stem and leaf eelworms, e.g., Ditylenchus dipsaci, Ditylenchus destructor, Pratylenchus neglectus, Pratylenchus penetrans, Pratylenchus goodeyi, Pratylenchus curvitatus and Tylenchorhynchus dubius, Tylenchorhynchus claytoni, Rotylenchus robustus, Heliocotylenchus multicinctus, Radopholus similis, Belonolaimus longicaudatus, Longidorus elongatus, and Trichodorus primitivus.

The active ingredients may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 2 is intimately mixed with 95 parts by weight of particulate kaolin. A dust is obtained containing 5% by weight of the active ingredient.

II. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 2 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 2 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 20 parts by weight of compound no. 2 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The active ingredient concentrations in the ready-to-use formulations may vary within a wide range; generally, they are from 0.0001 to 10%, and preferably from 0.01 to 1%. The active ingredients may also be successfully used in the ultra-low-volume (ULV) process, in which it is possible to apply formulations containing more than 95 wt % of active ingredient, or even the active ingredient without additives.

When agents containing the compounds according to the invention are used in the open, the amount of active ingredient employed is from 0.2 to 10, and preferably from 0.5 to 2, kg/ha.

Oils of various types, herbicides, fungicides, other pesticides and bactericides may be added to the active ingredients, if desired immediately before use (tankmix), in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-diethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethylphosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethylphosphonodithioate, O,O-diethyl-β2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethylpyrophosphoramide, O,O,O,O-tetraethyldithiopyrophosphate, S-chloromethyl-O,O-diethylphosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5[4H]-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, alpha-cyano-3-phenoxybenzyl(±)-cis,trans-2,2-dimethyl-3-(2,2-dichlorovinyl)-cyclopropanecarboxylate, (s)-alpha-cyano-3-phenoxybenzyl-cis(1R,3R)-2,2-dimethyl-3-(2,2-dibromovinyl)-cyclopropanecarboxylate, 3,4,5,6-tetrahydrophthalimidoethyl-DL-cis,trans-chrysanthemate, 2-methyl-5-(2-propynyl)-3-furylmethyl-chrysanthemate, and alpha-cyano-3-phenoxybenzyl-alpha-isopropyl-4-chlorophenylacetate.

MANUFACTURING EXAMPLE

N-{2-[4-(1-methylprop-1-yloxy)-phenoxy]-ethyl}-cyclopropanecarboxamide

At 5° C., 3.4 g of cyclopropanecarboxylic chloride was dripped into a solution of 6.5 g of 2-[4-(1-methylprop-1-yloxy)-phenoxy]-ethylamine and 3.5 g of triethylamine in 100 ml of absolute methylene chloride. After the mixture had been stirred for 8 hours it was poured onto 200 g of ice/water and the resultant solution was adjusted to a pH of 2 with 2N aqueous hydrochloric acid. The aqueous phase was then extracted twice, each time with 50 ml of methylene chloride, and the combined organic phases were washed with saturated sodium carbonate solution and water, and dried over sodium sulfate. After removal of the solvent under reduced pressure and recrystallization from cyclohexane, there was obtained 6.4 g of N-{2-[4-(1-methylprop-1-yloxy)-phenoxy]-ethyl}-cyclopropanecarboxamide (compound no. 2); m.p.: 65°-68° C.

The compounds I listed in the tables below without any physical characteristics may be readily prepared from the corresponding starting materials and may be expected to have a similar action.

TABLE

Compound I

(I)

| Compound No. | R | X | m.p. [°C.] | $^1$H—NMR in CDCl$_3$ |
|---|---|---|---|---|
| 1 | 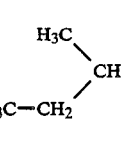 | O | 98-100 | |
| 2 | 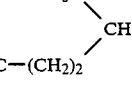 | O | 65-68 | |
| 3 | 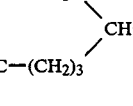 | O | | 6.84 (s) |
| 4 | 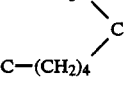 | O | 52-54 | |
| 5 | 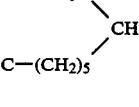 | O | 58-61 | |
| 6 | 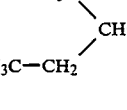 | O | | |
| 7 | 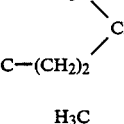 | S | 82-84 | |
| 8 | 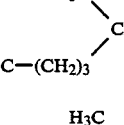 | S | | |
| 9 | 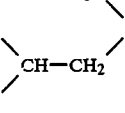 | S | | |
| 10 | 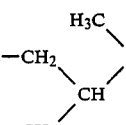 | O | | 6.80 (s) |
| 11 |  | O | | 6.81 (s) |

TABLE-continued

Compound I (I)

Cyclopropanecarboxamide structure: cyclopropyl-C(=O)-NH-CH₂CH₂-O-(p-phenylene)-X-R

| Compound No. | R | X | m.p. [°C] | ¹H—NMR in CDCl₃ |
|---|---|---|---|---|
| 12 | (H₃C)₂CH-CH(CH₃)- (i.e., H₃C-CH(CH₃)-CH(CH₃)-, shown as isobutyl-like branched) | S | | |
| 13 | H₂C=CH-CH(CH₃)- | O | | |
| 14 | H₂C=CH-CH₂- | O | | |
| 15 | Cl₂C=CH-CH₂- | O | | |
| 16 | (H₃C)₂C=C(CH₃)- with CH branch | O | | |
| 17 | (H₃C)₂C=C(CH₃)- with CH branch | S | | |
| 18 | cyclobutyl | O | | |
| 19 | cyclopentyl | O | | |
| 20 | cyclohexyl | O | 90–93 | |
| 21 | cyclopropylmethyl | O | | |
| 22 | cyclohexylmethyl | O | | |
| 23 | 2,2-dichlorocyclopropylmethyl | O | 65–68 | |
| 24 | 2,2-dichlorocyclopropylmethyl | S | | 6.72 and 7.48 (2d) |
| 25 | HC≡C-CH₂- | O | 119–121 | |
| 26 | Cl-C≡C-CH₂- | O | | |
| 27 | HC≡C-CH(CH₃)- | O | 115–117 | |
| 28 | H₃C-CH=C(CH₃)-CH(CH₃)- (1-methyl-2-butenyl type) | O | | |
| 29 | (H₃C)₂CH-CH₂- | O | 94–96 | |
| 30 | (H₃C)₂CH-(CH₂)₂- | O | 110–112 | |
| 31 | (H₃C)₂CH-CH₂- | S | | |
| 32 | (H₃C-CH₂)₂CH- | O | | 6.80 (s) |
| 33 | (F-CH₂)₂CH- | O | | |
| 34 | F₃C-CH₂- | O | | |
| 35 | 2-methylcyclopropyl (cyclopropane-CH(CH₃)-) | O | | |
| 36 | Cl-CH=CH-CH₂- | O | | |
| 37 | (H₃C)₃C- | O | 75–76 | |
| 38 | H₃C-CH₂-CH₂- | O | 99–100 | |
| 39 | H₃C-CH₂-CH₂-CH₂- | O | 100–102 | |
| 40 | H₃C- | O | 106–109 | |
| 41 | H₃C-CH₂- | O | 102–104 | |
| 42 | H₃C(CH₂)₄- | O | 102–104 | |
| 43 | (H₃C)₃C-CH₂-CH₂- | O | 62–65 | |
| 44 | (H₃C)₃C-CH₂-CH(CH₃)- | O | 57–61 | |
| 45 | H₃C-CH₂-CH(CH₃)-CH₂- | O | 54–60 | |
| 46 | (H₃C-CH₂)(H₃C-(CH₂)₂)CH- | O | | 6.80 (s) |

TABLE-continued

Compound I

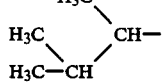

| Compound No. | R | X | m.p. [°C.] | $^1$H—NMR in CDCl$_3$ |
|---|---|---|---|---|
| 47 | (H$_3$C)$_2$CH—CH(CH$_3$)— [H$_3$C, H$_3$C-CH, H$_3$C-CH, CH—] | O | | 6.82 (s) |
| 48 | (H$_3$C)$_2$C=CH—CH$_2$— | O | 77-79 | |
| 49 | H$_3$C—CH(F)—CH(CH$_3$)— | O | | |
| 50 | Cl—CH$_2$—CH(CH$_3$)— | O | | |
| 51 | Cl—CH$_2$—CH$_2$—CH(CH$_3$)— | O | | |
| 52 | H$_3$C—O—CH(CH$_3$)—CH$_2$— | O | 69-73 | |
| 53 | H$_3$C—O—CH(CH$_3$)—CH—CH$_2$— | O | 95-97 | |
| 54 | H$_3$C—O—CH$_2$—CH(CH$_3$)— | O | | 3.40 (s) |
| 55 | H$_3$C—O—CH$_2$—CH$_2$— | O | 108-114 | |
| 56 | H$_3$C—O—CH$_2$—CH$_2$—CH(CH$_3$) | O | | 3.28 (s) |
| 57 | H$_3$C—O—CH$_2$—CH$_2$— | S | | 3.32 (s) |
| 58 | H$_3$C—O—CH$_2$—CH(CH$_3$)— | S | | 3.42 (s) |

USE EXAMPLES

In the following examples the action on pests of the compounds according to the invention was compared with that of the following prior art compounds:

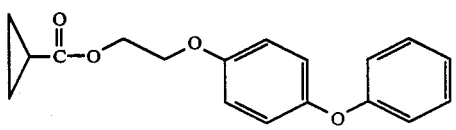

from DE-A-26 33 069

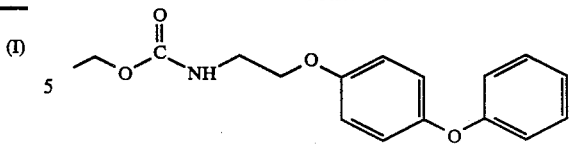

from EP-A-4334 and

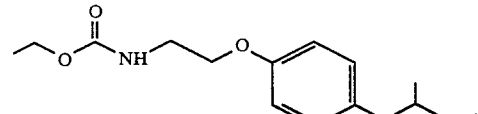

from EP-A-169 169.

The concentrations at which the investigated compounds achieved a 100% kill or inhibition are the minimum concentrations. At least one replicate was run for each concentration.

Breeding Experiment with Mosquito Larvae (*Aedes aegypti*)

The active ingredient formulations were added to 200 ml of tapwater and 20 to 30 mosquito larvae in the fourth larval stage were introduced. The vessels were kept at 25° C. Pupation and hatching of the imagoes, which took place after 10 to 12 days, were monitored. A powdered tropical fishfood was fed once during the observation period.

In this experiment, compound no. 2, at a rate of 0.03 ppm, achieved 100% kill, whereas comparative compound I' achieved a kill of 50% and comparative agent I'' a kill of 80%.

Breeding Experiment with Cotton Stainers (*Dysdercus intermedius*)

Moist quartz sand treated with solutions of the active ingredients was introduced into 1 liter jars and larvae of the fourth larval stage were kept on it at 25° C. The experiment was run until the following generation hatched. The imagoes were assessed for morphogenesis disturbances.

In this experiment, compound no. 2, at a rate of 1 ppm in the sand, achieved 80% kill, whereas comparative compound I' had no effect and comparative compound I'' exhibited a kill rate of 30%. Comparative compound I''' had to be used in a tenfold amount to achieve 80% kill.

Development Inhibition in *Prodenia litura* (Experiment on Treated Nutrient Medium)

100 g of the standard nutrient medium for Prodenia was filled into 250 ml beakers, and carefully mixed, while warm, with aqueous formulations of the active ingredients. After the medium had cooled, 10 caterpillars of the fourth larval stage were introduced into each vessel, and the vessels were kept at 23° C. The observation period extended up to hatching of the moths.

In this experiment, compound no. 2 achieved 100% kill at a rate of 0.3 ppm, 80% kill at a rate of 0.1 and 0.03, and 60% kill at a rate of 0.01 ppm. Comparative compound I' had no effect at all these rates. Comparative compound I'' achieved 100% mortality at 0.3, 0.1 and 0.03 ppm, but the kill dropped to 60% at a rate of 0.01 ppm.

Ovicidal Action on *Ceratitis capitata* (Mediterranean Fruit Fly)

20 to 30 eggs from 0 to 24 hours old were placed on a 5×5 cm filter paper in a closed vessel; half a roll of absorbent cotton moistened with water and a ball of mashed carrots 1.5 cm in diameter were introduced. The filter paper was moistened with 1.5 ml of the candidate solution and kept at 25° to 26° C. during the 5 to 6 days the experiment was run. Hatching and development of the larvae were assessed.

In this experiment, compound no. 2, at a rate of 1%, had the same action as comparative compound I''. Compound no. 2 retained its action at 0.3%, whereas compound I'' was ineffective. Comparative compound I' was ineffective at all the rates investigated.

In the following examples, the action on pests of compounds 3, 10 and 30 is compared with that of the following prior art compound (I$^v$)

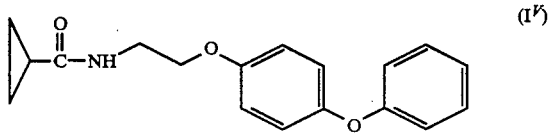

The concentration at which the compounds investigated achieve 100% kill or inhibition are the minimum concentrations. At least one replicate was run for each concentration.

Breeding Experiment with *Dysdercus intermedius* (Cotton Stainer)

Moist quartz sand treated with solutions of the active ingredients was introduced into 1 liter jars and larvae of the third larval stage were kept on it at 25° C. The experiment was run until the following generation hatched.

In this experiment, compounds nos. 10 and 30 achieved 100% kill at a rate of less than 0.5 ppm, whereas comparative compound (I$^v$) only achieved 100% kill at a rate of 1 ppm. In the case of compound no. 3, 4 ppm was required.

Ovicidal Action on *Dysdercus intermedius* (Cotton Stainer)

Pieces of double-sided adhesive tape were stuck to the top edge of plastic plant markers. 24 hours before commencement of the experiment, eggs of the cotton stainer were attached to the adhesive strips. The eggs were then treated with aqueous formulations of the active ingredients. The markers were then placed in plastic trays (adhesive strip at the top). Half a roll of absorbent cotton was moistened with water and placed in each beaker to prevent drying out. Assessment took place after the control bugs hatched (after about 8 days). The hatch inhibition in % was assessed.

In this experiment, compound 30 and comparative agent (I$^v$) were ineffective at 1000 ppm, whereas compounds 3 and 10 inhibited hatching to a degree of 80% at far lower concentrations (200 ppm and less).

Development Inhibition in *Prodenia litura* (Experiment on Treated Nutrient Medium)

100 g of the standard nutrient medium for Prodenia was filled into 250 ml beakers, and carefully mixed, while warm, with aqueous formulations of the active ingredients. After the medium had cooled, 5 caterpillars of the third larval stage were introduced into each vessel, and the vessels were kept at 25° to 26° C. The observation period extended up to hatching of the moths.

In this experiment, concentrations of 0.02 ppm of (I$^v$), 0.02 and 0.04 ppm (compounds 3 and 10) and 0.1 ppm (compound 30) achieved 100% kill.

Breeding Experiment with *Tribolium castaneum* (Red Flour Beetle)

10 g of wheat flour was introduced into 250 ml yoghurt bottles and mixed with the appropriate amount of the active ingredients as a dust formulation. 20 beetles were introduced and kept in the bottles for 14 days until they had laid eggs, and were then removed. The experiment was run until the next generation hatched. The temperature was kept at 24° C.

In this experiment, compounds 3, 10 and 30 according to the invention achieved 100% kill at a concentration of 10 ppm, whereas the comparative compound only achieved 80% kill at a concentration four times higher.

Breeding Experiment with *Ceratitis capitata* (Mediterranean Fruitfly)

The experiments were carried out in 100 ml plastic beakers containing 40 g of a nutrient medium consisting of carrot powder and water with added yeast. The active ingredient was stirred as an aqueous formulation into the mash, which was then inoculated with 100 to 200 fresh eggs. The beakers were kept closed at from 24° to 26° C. After about a week, hatching was assessed.

In this experiment, compound 3 achieved 100% kill at a rate of 10 ppm, whereas all other compounds including (I$^v$) were ineffective at a concentration ten times higher.

Breeding Experiment on Larvae of the Flour Moth (*Ephestia kuehniella*)

Wheat flour heavily infested with eggs of the flour moth was intimately mixed with the active ingredients. 10 g of the mixture was filled into 250-ml bottles, which were then kept at 25° C. The development of the larvae was assessed after 6 weeks.

In this experiment, all the compounds according to the invention achieved 100% kill, whereas comparative agent (I$^v$) only achieved 75% kill at a concentration four times higher.

We claim:

1. Cyclopropanecarboxamides of the formula I

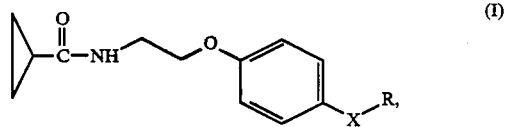

where the substituents have the following meanings:
R is selected from the group consisting of $C_1$–$C_{12}$-alkyl, $C_2$–$C_{12}$-alkenyl, $C_2$–$C_{12}$-alkynyl, $C_1$–$C_{12}$-haloalkyl, $C_2$–$C_{12}$-haloalkenyl, $C_2$–$C_{12}$-haloalkynyl, $C_3$–$C_{12}$-alkoxyalkyl, $C_3$–$C_8$-cycloalkyl, $C_4$–$C_{12}$-cycloalkylalkyl, $C_3$–$C_8$-halocycloalkyl, $C_4$–$C_{12}$-halocycloalkylalkyl, $C_4$–$C_{12}$-cycloalkylhaloalkyl or $C_4$–$C_{12}$-halocycloalkylhaloalkyl and
X is selected from the group consisting of oxygen or sulfur.

2. A pesticide containing a pesticidally effective amount of a cyclopropanecarboxamide of the formula I as set forth in claim 1, in admixture with a suitable carrier therefor.

3. A process for combating pests which comprises: applying to the pests or to their habitat a pesticidally effective amount of a cyclopropanecarboxamide of the formula I as set forth in claim 1.

4. A cyclopropanecarboxamide of the formula I as set forth in claim 1, where R is $C_3$–$C_{12}$-alk-2-yl, $C_3$–$C_{12}$-alkoxyalk-2-yl, $C_3$–$C_{12}$-alken-2-yl or $C_4$–$C_{12}$-alkyn-2-yl, and X is oxygen.

5. A cyclopropanecarboxamide of the formula I as set forth in claim 1, where R denotes 1-methylprop-1-yl and X is oxygen.

* * * * *

UNITED STATES PATENT AND TRADEMARK OFFICE
CERTIFICATE OF CORRECTION

PATENT NO. : 4,960,796

DATED : October 2, 1990

INVENTOR(S) : Hans-Juergen NEUBAUER et al.

It is certified that error appears in the above-identified patent and that said Letters Patent is hereby corrected as shown below:

IN THE ABSTRACT:

line 7: "$C_4$-$C_{12}$-halocycloalkylalhaloalkyl" should read --$C_4$-$C_{12}$-halocycloalkylalkyl--

Signed and Sealed this

Twenty-fourth Day of December, 1991

Attest:

HARRY F. MANBECK, JR.

Attesting Officer

Commissioner of Patents and Trademarks